United States Patent [19]

Baker et al.

[11] 4,321,330
[45] Mar. 23, 1982

[54] TISSUE CULTURE DEVICE

[76] Inventors: Fraser L. Baker, 6227 Orange St., Los Angeles, Calif. 90048; John H. Baumann, 836 Wartman Ave., Kingston, Ontario, Canada, K7M 4M5

[21] Appl. No.: 137,275

[22] Filed: Apr. 4, 1980

[51] Int. Cl.³ .......................... C12M 1/20; C12M 3/00
[52] U.S. Cl. ..................... 435/301; 435/298; 435/299; 435/300; 435/284
[58] Field of Search ............... 435/284, 285, 286, 297, 435/298, 299, 300, 301

[56] References Cited

U.S. PATENT DOCUMENTS

| 2,348,448 | 5/1944 | Brewer | 435/298 |
|---|---|---|---|
| 2,971,892 | 2/1961 | Carski | 435/298 |
| 3,097,070 | 7/1963 | Aldrich et al. | 435/297 X |
| 3,158,553 | 11/1964 | Carski | 435/298 |
| 3,179,574 | 4/1965 | Harrison | 435/297 |
| 3,203,870 | 8/1965 | Andelin | 435/298 |
| 3,499,825 | 3/1970 | Falcone et al. | 435/297 |
| 3,537,956 | 11/1970 | Falcone et al. | 435/297 X |
| 3,630,849 | 12/1971 | Land et al. | 435/297 X |
| 3,816,264 | 6/1974 | Winter et al. | 435/298 |
| 4,012,288 | 3/1977 | Lyman et al. | 435/298 X |

*Primary Examiner*—Robert J. Warden

[57] ABSTRACT

A disposable tissue culture device, particularly for aerobic cultures, comprising a tissue culture dish containing at least one shallow culture chamber for the growth of microorganisms, and a cover for the culture dish to prevent the entrance of contaminants, the cover being in contact with the contents of each culture chamber over the entire culture chamber to provide optimal viewing of each culture chamber by light microscopy through a transparent cover window, standoffs being provided between the cover and the culture dish to assure atmospheric communication between each culture chamber and ambient atmosphere, minimum annular space being provided between the cover and upper edge of each culture chamber to maintain an almost enclosed, constant volume in each culture chamber to hold the culture stable during culturing, handling and vibration, yet permit the culture to breathe. The transparent cover window portion of the cover enclosing the contents of each culture chamber is substantially flat, and has a slight convex, upward curve on the inside surface adjacent to the edge to permit egress of bubbles due to de-gassing of fluid in each culture chamber. An annular fluid reservoir, provided around the upper edge of each culture chamber, permits compensation for evaporation of fluid from the culture and provides a tolerance on the filling volume. Lift lugs are provided on opposite sides of the dish extending outward beyond the cover and upward to facilitate moving the culture dish without disturbing the cover located thereon, the lift lugs extending only partway around the dish to permit easy removal and replacement of the cover for administration of specimens and other ingredients to each culture chamber.

10 Claims, 6 Drawing Figures

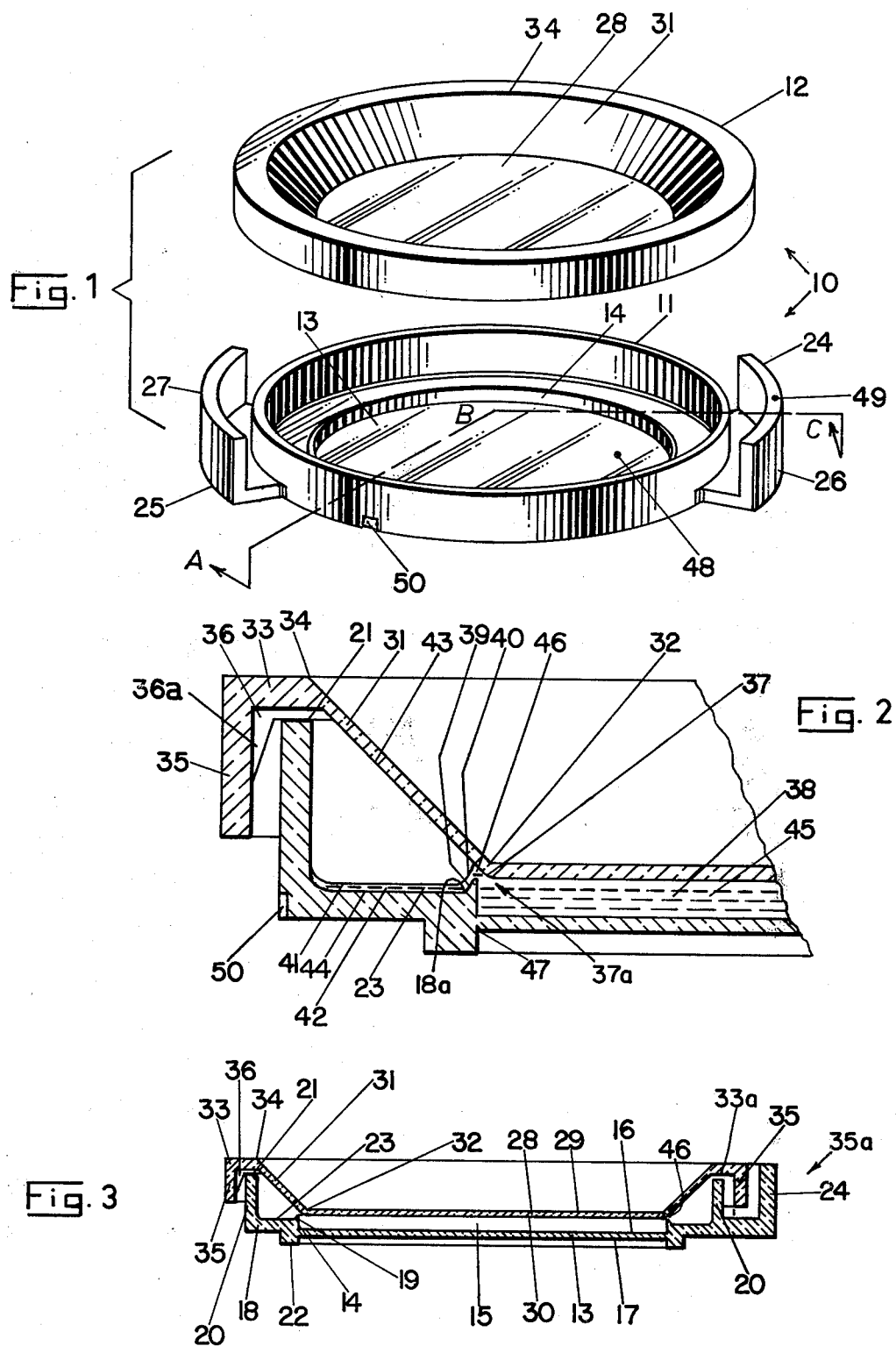

TISSUE CULTURE DEVICE

This invention relates to a tissue culture device of a type especially suited for growing aerobic microorganisms and for optimal viewing of these microorganisms using light microscopy.

BACKGROUND AND PRIOR ART

Generally for culturing microorganisms, two types of medium are in common use; liquid medium in which the microorganisms settle on the bottom surface of the culture dish, and semi-solid medium in which the microorganisms are evenly dispersed throughout the culture medium. Two configurations of light microscopes are in common use: the upright and the inverted microscope. The upright microscope has its objective lens above the specimen and is generally used to observe specimens placed on microscope slides, whereas the inverted microscope has its objective lens situated below the specimen and is generally used to observe microorganisms growing in culture. In order to obtain useful information from practically all types of renewing and mature cell populations, it is often desirable to observe living cell cultures in liquid medium, using an inverted microscope, or to observe living cell cultures in semi-solid medium, using an upright microscope. One use of this type of information and observation is in the treatment of cancer, where the efficacy of anti-cancer drugs on a particular patient's cancer cells can be assessed in tissue culture prior to treatment. Another use of this type of observation is in basic biological research wherein cell division and function can be studied at the level of the single cell.

Cultures performed in semi-solid medium in conventional culture dishes have the following limitations:

1. Since the cells are suspended throughout the entire volume of the culture medium at varying heights, constant focus adjustment of the microscope is necessary during observation, making quantitive observations tedious and time consuming.

2. Many of the cells under observation are sufficiently far removed from the objective lens of the microscope, (even using an inverted microscope) that high objective lens power cannot be used for observation.

These limitations may be overcome by using liquid culture medium in conjunction with an inverted microscope for observation. In liquid culture all the cells settle to the bottom of the dish in a monolayer and can be focused upon from below even using high objective lens power. Since all the cells lie in the same plane, once the plane is focused upon, no additional focusing is necessary. However, cultures performed in liquid medium in conventional culture dishes have the following limitations:

1. Cells are continuously moved about the bottom surface by the motion of the liquid medium, due to standing wave and convection currents.

2. There is mass movement in the culture upon handling, and spillage occurs readily with only slight tilting of the dish.

3. A meniscus is formed at the edge of the liquid culture medium, distorting the highly focused light from the light source passing through the upper surface of the liquid, making high resolution observation of cells, particularly toward the outside edges of the dish, very difficult and unreliable. Furthermore, the increased thickness of medium in the area of the meniscus results in an increase of cell density at the edge of the culture chamber. This leads to a high cell density in a region that cannot be well observed, a situation that is far from ideal.

Presently, culturing in semi-solid medium is in more common use than culturing in liquid medium, because no dish has hitherto been available that has been able to overcome the physical instability of liquid medium and of the cells in that medium. It is an object of this invention to provide a tissue culture device suitable for the observation of living cells and organisms while being cultivated in semi-solid or liquid medium, suitable for use with both upright and inverted light microscopes.

Another object of this invention is to provide a tissue culture device which contains the culture in an almost totally enclosed volume holding the culture stable by providing minimum free surface areas, thus preventing cell aggregation in certain areas, and mass movement upon handling of the dish.

Another object of this invention is to provide a tissue culture device able to compensate for evaporative water loss from the culture during extended culture periods.

Yet another object of this invention is to provide a tissue culture device which allows a reasonable tolerance in volume of the medium required to fill the fixed volume culture chamber.

Another object of this invention is to provide a tissue culture device with no optical distortion due to meniscus near the edge of the culture region.

Another object of this invention is to provide a tissue culture device containing more than one identical culture chamber, each with the above features.

The present invention solves the above problems by stabilizing the liquid medium in an almost totally enclosed fixed volume. This is accomplished by placing a window in contact with the entire top surface of the culture chamber.

For ease of explanation, the following will refer to a culture device having only one culture chamber, each culture chamber of a multiple chamber device being identical to each other.

In order to observe cells being cultured in semi-solid medium in conventional culture dishes it has been found necessary to use an inverted microscope in order to be able to place the objective lens closer to the cells being observed and thus achieve higher objective lens power observation than would be possible with an upright microscope. The present invention incorporates a transparent cover window that is lowered down to and in contact with the top surface of the culture chamber to permit observation of culture cells using an upright microscope at the same objective lens power as an inverted microscope. This is of advantage since there are many more upright microscopes currently in use than inverted microscopes.

Cells cultured in semi-solid medium are susceptible to vibration-induced oscillations since the support used to solidify the medium forms a gel, which is very resilient and responds to vibrations in the environment. Distortion due to meniscus, and aggregation of cells near the edge of the culture chamber occurs in semi-solid cultures in conventional culture dishes, as it does in liquid cultures. The present invention solves these problems involving semi-solid cultures by imparting a high degree of stability to the semi-solid medium, the surface of the upper window in contact with the medium greatly diminishing the ability of the medium to vibrate.

Although the present invention offers particular advantages for the observation of liquid cultures using an inverted microscope and for the observation of semi-solid cultures using an upright microscope, it may also be used for the observation of semi-solid cultures with an inverted microscope and for the observation of liquid cultures with an upright microscope.

Other objects and features of the invention will become apparent from the following description of the invention taken in conjunction with accompanying drawings in which:

FIG. 1 is a perspective view of a tissue culture dish and cover therefor, embodying this invention, separated from each other and illustrating a preferred form of the invention containing one culture chamber.

FIG. 2 is a partial, cross-sectional view of the tissue culture device shown in FIG. 1, taken on the line A—B, the tissue culture dish containing an organism-supporting medium, illustrating the meniscus formed, peculiar to this invention, and the almost complete enclosure of the medium within the culture chamber, between the culture chamber and the transparent viewing window of the cover.

FIG. 3 is a cross-sectional elevation taken along line A—B—C of FIG. 1 showing the cover located in place on the tissue culture dish.

DESCRIPTION OF THE PREFERRED EMBODIMENT

Figure 4:
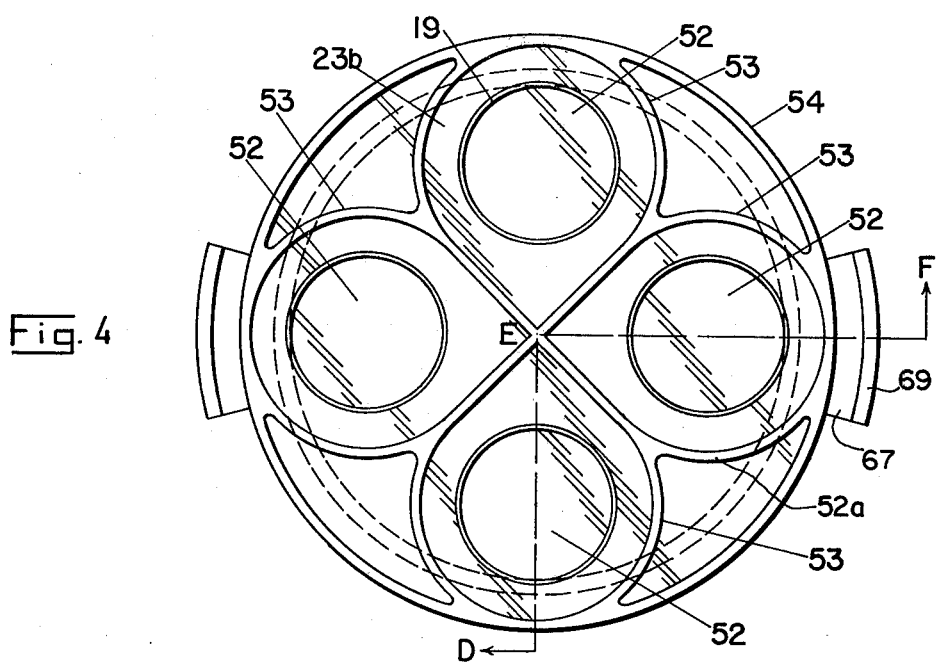
FIG. 4 is a plan view of a tissue culture dish containing multiple culture chambers, illustrating four identical culture chambers located in the tissue culture device.

Referring to the drawings, FIGS. 1, 2, and 3 show a substantially circular tissue culture device 10 as a preferred embodiment of this invention which however may equally well be made in a non circular configuration such as a square or rectangular form or any other form desired. The tissue culture device 10 comprises a tissue culture dish 11 and a cover 12, dish 11 having a transparent base window 13 surrounded by an annular vertical wall 14 forming a culture chamber 15, transparent base window 13 being substantially planar and having an upper surface 16 and a lower surface 17. An annular peripheral flange 18 extends outwardly from the exterior of wall 14, slightly below an upper edge 19 of wall 14, flange 18 being connected to wall 14 by a concave curved edge 18a to provide means to facilitate rise of fluid to upper edge 19 flange 18 having an upward extending, annular, peripheral outer wall 20 extending upward to a cover-supporting edge 21. A peripheral, annular, flat rim 22 depends downward from flange 18, slightly below and peripherally around lower surface 17 of base window 13 providing a shallow recess in surface 17 to prevent lower surface 17 from being scratched or damaged by any surface upon which culture dish 11 is placed, and to provide a matrix for punching out base 13 from dish 11. A peripheral, annular U-shaped flange 18 is formed around culture chamber 15 by wall 14, flange 18 and annular outer wall 20 and provides a shallow fluid reservoir 23. Two oppositely disposed lugs 24 and 25 extend outwardly from flange 18 and upwardly therefrom to form vertical lift lug portions 26 and 27.

Cover 12 comprises a transparent bottom window 28 having an upper surface 29 and a lower surface 30. A peripheral wall 31 extends outwardly and upwardly from peripheral edge 32 of bottom window 28. An annular flange 33 extends outwardly from an upper edge 34 of wall 31, flange 33 having a peripheral, downwardly extending wall 35. It will be seen in FIG. 3 that lug 24, in conjunction with wall 20, is adapted to freely straddle wall 35 of cover 12.

Referring to FIGS. 2 and 3, at least three standoffs 36 are located beneath flange 33 with free air space 33a between each standoff 36 and between cover supporting edge 21 and cover 12, to locate cover 12 upon culture dish 11 in proper relation to each other. It will be realized that these standoffs may equally well be upwardly extending from wall 20 of culture dish 11 instead of downwardly depending from cover 12. Free air spaces 33a constitute means for providing access for ambient atmosphere 35a to fluid reservoir 23 by permitting ambient atmosphere 35a, surrounding tissue culture device 10, to pass through air spaces 33a to fluid reservoir 23. Standoffs 36 have a form suitable to also provide means for centering cover 12 horizontally over culture dish 11, in the preferred configuration comprising at least 3 downward depending ribs 36a. Lower boundary edge 37 between the lower surface 30 of bottom window 28 of cover 12 and wall 31 has a convex curve configuration, as shown at 37a, to facilitate flow of fluid from below window 28, along lower surface 30 to fluid reservoir 23 and thereby facilitate egress of bubbles, formed in a fluid medium 38, as shown in FIG. 2, located in culture dish 11, into reservoir 23. Upper edge 19 of annular, vertical wall 14 is formed into a narrow lip 39.

A meniscus 40 is formed between fluid surface 41 of fluid 42 in fluid reservoir 23 and lower surface 43 of wall 31, and allows exchange of gaseous nourishment and waste products between culture chamber 15 and ambient atmosphere surrounding tissue culture device 10, providing atmospheric communication between medium 38 and ambient atmosphere so that culture in medium 38 can breathe, this exchange taking place through the annular free surface of meniscus 40.

Meniscus 40 exists during the whole culture period while there is fluid remaining in reservoir 23 and maintains fluid contact between fluid 45 in culture chamber 15 and fluid 42 in fluid reservoir 23 so that the fluid 42 can be drawn into the area of meniscus 40 from fluid reservoir 23 to compensate for fluid loss due to evaporation in the area of meniscus 40.

Meniscus 40 will rise a fixed distance above fluid surface 41, depending on wettability of material used in cover 12 and type of fluid medium 38. The higher fluid surface 41 is in reservoir 23, the higher up meniscus 40 will rise on surface 43 of wall 31. In order to maintain a meniscus 40 at all times while there is fluid in reservoir 23, the distance between bottom surface 44 of reservoir 23 and lower surface 43 of wall 31, in the area where these surfaces are closest to each other, must be less than the rise height of meniscus 40 under above conditions. This ensures that meniscus 40 will remain unbroken until all of fluid 42 is drawn out of reservoir 23. As an example, tests have shown that meniscus 40 will rise to approximately three thirty-seconds of an inch before breaking, if the tissue culture device is composed of the type of plastic normally used for disposable tissue culture dishes.

The function of lip 39 is to provide a narrow, annular gap 46 between wall 14 of culture chamber 15 and lower surface 43 of cover wall 31. As fluid 42 evaporates from fluid reservoir 23, the height of fluid surface 41 is lowered in fluid reservoir 23, thereby lowering meniscus 40 and drawing it closer to gap 46. Due to the comparatively small quantity of fluid 42 in reservoir 23, fluid 42 may not be removed evenly from all parts of fluid reservoir 23 as it evaporates. In regions where fluid 42 dries up first, meniscus 40 will be drawn into annular gap 46, bridging gap 46. Meniscus 40 will become a free surface, bridging gap 46, having a high surface tension due to the narrowness of gap 46, and will hold the free surface in place in gap 46, keeping it from entering culture chamber 15.

The same conditions as above may occur upon culture device 10 being tilted; for instance, upon culture device 10 being moved from one place to another. Although there is ample fluid in reservoir 23, upon tilting, this fluid is all in one portion of reservoir 23. In this condition, gap 46 holds the annular free surface of medium 38 in place in gap 46, keeping it from entering culture chamber 15.

Figure 5:
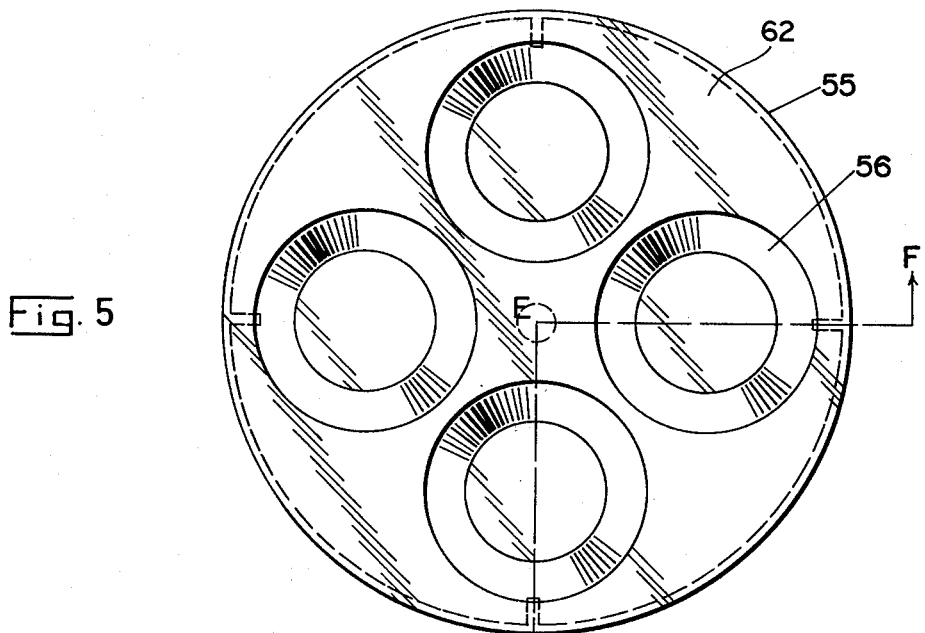
FIG. 5 is a plan view of a cover for the multiple culture chamber tissue culture dish shown in FIG. 4.
Figure 6:
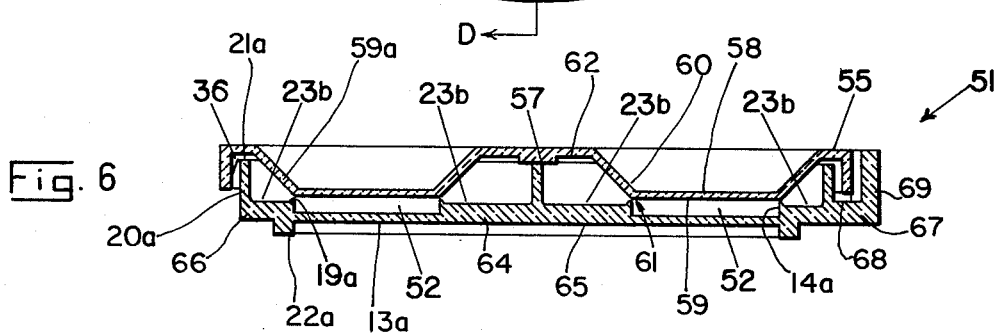
FIG. 6 is a cross-sectional elevation taken along lines D—E—F of FIGS. 4 and 5 showing the multiple chamber cover located in place on the multiple chamber tissue culture dish.

Referring to FIGS. 4, 5 and 6, a multiple chamber tissue culture device 51 is shown containing four tissue culture chambers 52, although it will be understood that the multiple chamber tissue culture device could be made with 2 or more culture chambers 52, each tissue culture chamber 52 being identical to culture chamber 15 shown in FIGS. 1, 2, and 3, each culture chamber 52 having a base window 13a surrounded by an annular vertical wall 14a having an upper edge 19a ending in a lip 19 and an annular fluid reservoir 23 to provide four miniature tissue culture dishes 53 located within culture dish 54, each miniature tissue culture dish 53 being separate from each other dish 53. All culture dishes 53 being joined together by a common circular flange 64 extending outwardly from the exterior of walls 14a to an annular, peripheral outer wall 20a, extending upward from flange 64 to a cover supporting edge 21a. A flat peripheral annular rim 22a depends downwards from flange 64, slightly below lower surface 65 and peripherally therearound, providing a shallow recess in lower surface 65. A secondary annular wall 52a is located on flange 64, externally of and surrounding each culture chamber 52, secondary annular wall 52a extending up to a short distance from top plate 62 of cover 55. A peripheral, upstanding u-shaped flange 66 is formed around each culture chamber 52 by wall 14a, flange 64 and secondary annular wall 52a to form fluid reservoirs 23b. Two oppositely disposed lugs 67 extend radially outward from flange 64 at base 68 of wall 20a to a location beyond downward depending outer wall 63 of cover 55, each lug 67 having an upward extending handle portion 69 extending up outside outer wall 63 of cover 55.

Cover 55 for multiple tissue culture dish 54, shown in FIG. 5 comprises four dish shaped culture chamber covers 56, each having a substantially flat bottom window 58 with a lower surface 59 and a peripheral, upwardly extending wall 59a extending from peripheral edge 60 of bottom window 58, wall 59a being connected to lower surface 59 by a convex curve 61. All covers 56 are joined together by a common substantially planar cover top plate 62, in the illustrated example of a circular configuration, bordered by a peripheral, downwward depending annular outer cover wall 63. At least three standoffs 36b are located beneath top plate 62 to locate cover 55 on culture device 51 in proper relation to each other and to provide free air space between cover 55 and culture device 51 to permit access to ambient atmosphere to culture dishes 53.

For ease of explanation, the following will refer to a tissue culture device having only one tissue culture chamber, the same features being valid for a tissue culture device containing more than one tissue culture chamber.

In use, a fixed volume of liquid medium or semi-solid medium containing microorganisms to be cultured is poured into culture chamber 15 and fluid reservoir 23 to fill both of these to a suitable height relative to lip 39, whereafter cover 12 is placed on culture dish 11 in such a way that standoffs 36 locate on support edge 21 of culture dish 11. Relative position between cover 12 and culture dish 11 will be such that lower surface 30 of cover 11 will have its complete surface in contact with medium 38, meniscus 40 being formed between fluid surface 41 and lower surface 43 of wall 31. A fixed volume of medium is thereby substantially fully enclosed in culture chamber 15 by lower surface 30, meniscus 40, wall 14, and base window 13, medium 38 thereby being held substantially entrapped and not free to move during handling or when subjected to vibration, tilting, and the like. Medium 38 is in atmospheric communication with ambient atmosphere through meniscus 40 and evaporation of medium 38 in the area of meniscus 40 is compensated for by fluid 42 in reservoir 23 thus retaining a full volume in culture chamber 15 at all times during the culture period.

The ability of fluid reservoir 23 to maintain meniscus 40 at varying volumes of fluid in reservoir 23 allows for tolerance in initially filling the correct volume of medium into culture chamber 15, thereby facilitating such filling by not requiring an absolutely accurate amount of medium 38 to be inserted into culture chamber 15 during each filling operation, yet maintains an exact predetermined volume of medium 38 in culture chamber 15 upon cover 12 being properly located on culture dish 11. Such an exact volume is important, for instance, for quantitive analysis, of cultures in medium 38, culture cell density also remaining constant due to culture cells settling to the bottom of medium 38 in culture chamber 15 and in reservoir 23, replacement fluid drawn up to meniscus 40 to replace evaporated fluid, being taken from fluid 42 in reservoir 23 above culture cells that have settled on the bottom 44 of reservoir 23, the replacement fluid therefore not containing any further culture cells.

Convex curve on edge 37 on the boundary between lower surface 30 of cover window 28 and lower surface 43 of wall 31 will permit egress of bubbles, from culture chamber 15 to reservoir 23, such bubbles being formed by degassing of fluid in culture chamber 15, for instance, as culture medium 38 warms up to ambient temperature, without breaking the formed meniscus 40.

Windows 28 and 13 are both planar and transparent and are both in intimate contact with medium 38, thereby permitting viewing of cultures in culture medium 38 from the top by an upright microscope and from the bottom by an inverted microscope. When the tissue culture device is utilized in conjunction with an inverted microscope, comparatively high objective lens power may be used for observation, and the close relative placement of windows 28 and 13 facilitates the use of highly focused light from a light source passing through the upper surface of the medium without distortion since meniscus 40 is formed outside the observation area.

Utilization of the tissue culture device in conjunction with an upright microscope is facilitated by cover window 28, in the present invention, being lowered down in cover 12 to a location substantially close to upper surface 16 of base window 13, thereby permitting comparatively higher objective lens power to be utilized for observation of culture cells in medium 38, than would be possible using a conventional type of cover, highly focused light from a light source passing through base window 13 and medium 38 without distortion since meniscus 40 is formed outside the observation area.

Base window 13 may be supplied with a peripheral groove 47, formed into base window 13 to provide means to facilitate detachment of base window 13 from culture dish 11, for instance, by punching base window 13 out after completion of culture period to obtain a permanent stained record; or base window 13 may be made suitably thin; for instance, less than one millimeter thick, to facilitate such a punching out operation.

Means for referencing specific culture locations on base window 13 may comprise at least one referencing mark 48 located on upper surface 16 of base window 13, which will be in focus during examination of culture cells thereon, for instance, for referencing moving cells or multiplying cells in relation to base window 13. One or both of lugs 24 and 25 may be supplied with locating marks 49 to facilitate locating and relocating tissue culture device 10 in same repeat position, for instance, on a microscope stage. A notch 50 may be located on dish 11 in outer annular wall 20 to correspond with a locating pin on a microscope stage or the like for this same purpose.

It will be understood that although specific embodiments of the invention have herein been described and illustrated, the invention also contemplates variations in design and method as may hold within the scope of the appended claims.

What is claimed is:

1. A tissue culture device comprising in combination a cover and a culture dish, said cover comprising a substantially flat, transparent bottom window having a lower surface and a peripheral edge, an inverted, peripheral, U-shaped flange on said bottom window having an inner wall extending upward from said peripheral edge of said bottom window and a downward depending outer wall, means to facilitate flow of fluid along said lower surface of said bottom window into said inverted U-shaped flange comprising a convex curve on said peripheral edge of said bottom window connecting said lower surface of said bottom window with said inner wall, means for centering said cover on said culture dish comprising at least three downwardly depending ribs located within said inverted U-shaped flange, standoff means for spacing said cover and said culture dish a predetermined distance apart from one another, said culture dish comprising a substantially flat base window having an upper surface and a lower surface, said base window having a peripheral, annular, vertically upward extending wall, said wall having an upper edge ending in a narrow lip, an upstanding, peripheral, U-shaped flange surrounding said vertically upward extending wall and forming a shallow fluid reservoir therearound, said transparent base window and said vertically upward extending wall forming a culture chamber substantially centrally in said culture dish, said standoff means also comprising means for providing access for ambient atmosphere to said fluid reservoir, an annular, peripheral outer wall of said upstanding U-shaped flange extending upward beyond said lip, said upward extending, outer wall having an upper supporting edge, said cover being adapted to rest on said upper supporting edge, said inverted U-shaped flange of said cover bridging said upward extending outer wall of said culture dish, said upward extending outer wall being of a height suitable to provide a predetermined narrow gap between said lip and said lower surface of said transparent bottom window of said cover, at least 2 oppositely disposed handling lugs extending radially outward from base of said outer wall of said culture dish to a location beyond said downward depending outer wall of said cover, each said lug having an upward extending portion extending up outside said cover, said lugs being adapted to permit said culture dish to be grasped and moved without disturbing said cover, located on said culture dish, means to facilitate rise of fluid in said reservoir toward said lip, means to facilitate detachment of said base window from said culture dish, means for referencing specific culture locations on said base window and means for locating and re-locating said culture dish in same repeat position on a microscope stage.

2. A tissue culture device as claimed in claim 1, in which said standoff means comprises at least 3 downwardly depending standoffs inside said inverted peripheral U-shaped flange of said cover, each said standoff having a downwardly depending rib adapted to center said cover over said culture dish, said means for providing access for ambient atmosphere, surrounding said culture device, into said fluid reservoir comprising said standoffs being spaced apart to provide a partial, peripheral free air space between said supporting edge of said culture dish and said cover adapted to permit ambient atmosphere, surrounding said culture device, to freely pass through said free air space into said fluid reservoir.

3. A tissue culture device as claimed in claim 1, in which said standoff means comprises at least 3 standoffs located on said supporting edge of said outer wall of said culture dish, each said standoff having an outward extending rib adapted to center said cover on said culture dish, said means for providing access for ambient atmosphere, surrounding said culture device, into said fluid reservoir comprising said standoffs being spaced apart to provide a partial, peripheral free air space between said supporting edge of said culture dish and said cover, adapted to permit ambient atmosphere, surrounding said culture device, to freely pass through said free air space into said fluid reservoir.

4. A tissue culture device as claimed in claim 1, in which said base window of said culture dish has a relatively shallow recess in said lower surface thereof, formed by a flat, peripheral, annular rim depending downward from said upstanding U-shaped flange of said culture dish, slightly below and peripherally around said lower surface of said base window, said means to facilitate detachment of said base window from said culture dish comprising said base window having a peripheral groove located partway into said lower surface of said base window.

5. A tissue culture device as claimed in claim 1 in which said base window of said culture dish has a relatively shallow recess in said lower surface thereof, formed by a flat, peripheral, annular rim depending downward from said upstanding U-shaped flange of said culture dish, slightly below said lower surface of said base window and peripherally therearound, said base window being less than 1 millimeter thick to facilitate punching said base plate out of said culture dish internally of said rim with a hollow cylindrical punch.

6. A tissue culture device as claimed in claim 1 in which said upstanding U-shaped peripheral flange is connected to said peripheral, annular vertical wall of said dish by a concave curve within said fluid reservoir.

7. A tissue culture device as claimed in claim 1 in which said means for referencing specific locations on said base window comprises at least one permanent reference mark on said base window and said means for locating and relocating said culture dish in same repeat position on a microscope stage comprises at least one locating mark on at least one of said lugs.

8. A tissue culture device as claimed in claim 1 in which said tissue culture device is non-circular.

9. A tissue culture device as claimed in claim 1 in which said means for locating and relocating said culture dish in same repeat position on a microscope stage comprises at least one orientation notch in said outer wall of said culture dish.

10. A tissue culture device comprising in combination a multiple cover and a multiple tissue culture dish, said multiple cover comprising a plurality of dish shaped individual culture dish covers, each having a substantially flat transparent bottom window, each said bottom window having a lower surface and a peripheral edge, a peripheral wall extending upwards from said peripheral edge of each said bottom window to a common, substantially planar top plate, said peripheral wall being connected to said lower surface of said bottom window by a convex curve, all said individual culture dish covers being joined together by said top plate, said top plate being bordered by a peripheral, downward depending outer cover wall, said multiple tissue culture dish comprising a plurality of individual culture dishes, equal in quantity to said plurality of culture dish covers, each said individual culture dish comprising a base window surrounded by an annular, vertical wall having an upper edge ending in a narrow lip, all said individual culture dishes being joined together by a common flange, extending outwardly from each said vertical wall of each said culture dish, substantially at said base window, to an annular, peripheral outer wall extending upward from said flange, upper edge of said outer wall of said multiple tissue culture dish providing a support edge to support said multiple cover, at least 3 standoffs being located beneath said top plate to locate said multiple cover on said multiple tissue culture dish in proper relation thereto and to space said multiple cover and said multiple culture dish suitably apart to provide free air space therebetween to permit access for ambient atmosphere to all said individual culture dishes, a flat annular rim depending downward from said flange to provide a shallow recess in lower surface of said flange, each said annular vertical wall of said individual culture dish in conjunction with each said base window forming an individual culture chamber, each said culture chamber being surrounded by a secondary annular wall extending upward from said flange to a short distance below said top plate of said multiple cover upon said top plate being located on said multiple tissue culture dish, a fluid reservoir being formed around said individual culture chamber by said annular wall, said flange and said secondary annular wall, and at least two oppositely disposed lugs extending radially outward from said flange at base of said outwardly extending outer wall of said multiple tissue culture dish, to a location beyond said downward depending outer wall of said multiple cover, each said lug having an upward extending handle portion extending upward outside said downward depending outer wall of said multiple cover.

* * * * *